(12) United States Patent
Govari

(10) Patent No.: US 11,399,735 B2
(45) Date of Patent: Aug. 2, 2022

(54) NONLINEAR ELECTRIC FIELD LOCATION SYSTEM

(71) Applicant: Biosense Webster (Israel) Ltd., Yokneam (IL)

(72) Inventor: Assaf Govari, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 1029 days.

(21) Appl. No.: 16/059,177

(22) Filed: Aug. 9, 2018

(65) Prior Publication Data

US 2020/0046250 A1 Feb. 13, 2020

(51) Int. Cl.
  *A61B 5/06* (2006.01)
  *A61B 34/20* (2016.01)
  *A61B 5/287* (2021.01)

(52) U.S. Cl.
  CPC .............. *A61B 5/062* (2013.01); *A61B 5/063* (2013.01); *A61B 5/287* (2021.01); *A61B 34/20* (2016.02); *A61B 2034/2051* (2016.02)

(58) Field of Classification Search
  CPC ......... A61B 5/062; A61B 5/063; A61B 5/068; A61B 5/6859; A61B 34/20; A61B 2560/0238; A61B 18/1492
  See application file for complete search history.

(56) References Cited

U.S. PATENT DOCUMENTS 5,391,199 A   2/1995  Ben-Haim
5,577,509 A * 11/1996  Panescu ................. A61B 5/287
                                                                  600/508
5,697,377 A   12/1997  Wittkampf
(Continued)

FOREIGN PATENT DOCUMENTS

WO    9605768 A1    2/1996

OTHER PUBLICATIONS

Extended European search report for corresponding European patent application No. EP 19190763.3, dated Dec. 6, 2019.
(Continued)

*Primary Examiner* — Thaddeus B Cox
(74) *Attorney, Agent, or Firm* — Notaro, Michalos & Zaccaria P.C.

(57) ABSTRACT

A method includes, in a calibration phase, positioning a calibration-tool, including a mapping-electrode and a sensor of a location-measuring system, in an organ. The calibration-tool is tracked at different positions in the organ using the location-measuring system. A set of calibration data points is generated at the respective different positions, each calibration data point including signal-values obtained using the mapping-electrode and a corresponding position measurement of the sensor by the location-measuring system. The method further includes, in an investigation phase that is subsequent to the calibration phase, positioning an investigation-tool at a location in the organ. The signal-values at the location are measured using a mapping-electrode of the investigation-tool. Using a subset of the calibration data points, coordinates of the location are determined by deriving a respective nonlinear relation between the signal-values obtained using the mapping-electrode of the investigation-tool, and the coordinates of the location and solving the nonlinear relation.

5 Claims, 2 Drawing Sheets

(56) References Cited

U.S. PATENT DOCUMENTS

| | | |
|---|---|---|
| 6,239,724 B1 | 5/2001 | Doron et al. |
| 6,332,089 B1 | 12/2001 | Acker et al. |
| 6,484,118 B1 | 11/2002 | Govari |
| 6,618,612 B1 | 9/2003 | Acker et al. |
| 6,690,963 B2 | 2/2004 | Ben-Haim et al. |
| 6,939,309 B1 | 9/2005 | Beatty et al. |
| 7,756,576 B2 | 7/2010 | Levin |
| 7,848,787 B2 | 12/2010 | Osadchy |
| 7,848,789 B2 | 12/2010 | Govari et al. |
| 7,869,865 B2 | 1/2011 | Govari et al. |
| 8,456,182 B2 | 6/2013 | Bar-Tal et al. |
| 2002/0065455 A1 | 5/2002 | Ben-Haim et al. |
| 2003/0120150 A1 | 6/2003 | Govari |
| 2004/0068178 A1 | 4/2004 | Govari |
| 2007/0016007 A1 | 1/2007 | Govari et al. |
| 2010/0079158 A1 | 4/2010 | Bar-Tal et al. |
| 2013/0006084 A1 | 1/2013 | Harley et al. |
| 2014/0187905 A1 | 7/2014 | Olson |
| 2016/0000357 A1* | 1/2016 | Harlev .................. A61B 5/063 600/424 |
| 2017/0135602 A1 | 5/2017 | Izmirli et al. |

OTHER PUBLICATIONS

Pending U.S. Appl. No. 15/966,514, filed Apr. 30, 2018.

Localisa, New Technique for Real-Time 3-Dimensional Localization of Regular Intracardiac Electrodes Fred H.M. Wittkampf, PhD et al.; Circulation. 1999;99:1312-1317.

\* cited by examiner

NONLINEAR ELECTRIC FIELD LOCATION SYSTEM

FIELD OF THE INVENTION

The present invention relates generally to electro-anatomical mapping, and particularly to intra-cardiac electro-anatomical mapping.

BACKGROUND OF THE INVENTION

Various techniques were proposed for deriving an accurate cardiac electro-anatomical map from intra-cardiac electro-anatomical measurements. For example, U.S. Patent Application Publication 2013/0006084 describes methods and systems for determining the position of an object, such as for tracking the position of one or more catheters in a patient's heart cavity. The system can use various methods to generate the local field maps. One exemplary way to generate either a local field model or a global field map is to generate a 3D grid with a resolution that fits the required accuracy of the tracking system and then apply interpolation techniques to the measured values. For example, the grid resolution may be 0.2 mm. An interpolation algorithm such as cubic interpolation can be used to interpolate the measured values onto the grid.

As another example, U.S. Patent Application Publication 2014/0187905 describes a system and method for determining a position of a medical device within a body. The system includes an electronic control unit that receives position signals from position sensors of a first type and a second type disposed on the device. The unit computes a spline connecting the position sensors of the first type responsive to the estimated positions for the sensors and estimates a spline position for the sensor of the second type along the spline. The unit generates maps between the spline position and determines actual positions for the sensors of the first type responsive to estimated position for the sensors of the second type and a composite map of the two maps.

U.S. Pat. No. 6,939,309 describes a mapping catheter that is positioned in a heart chamber, and active electrode sites that are activated to impose an electric field within the chamber. The blood volume and wall motion modulate the electric field, which is detected by passive electrode sites on the preferred catheter. Electrophysiology measurements, as well as geometry measurements, are taken from the passive electrodes and used to display a map of intrinsic heart activity. Various techniques for creating a shape are possible, including cubic spline fits, and best fit of an ellipsoid.

U.S. Pat. No. 5,697,377 describes a system and method for catheter location mapping, and related procedures. Three substantially orthogonal alternating signals are applied through the patient, directed substantially toward the area of interest to be mapped, such as patient's heart. A catheter is equipped with at least a measuring electrode, which for cardiac procedures is positioned at various locations either against the patient's heart wall, or within a coronary vein or artery. A voltage is sensed between the catheter tip and a reference electrode, preferably a surface electrode on the patient, which voltage signal has components corresponding to the three orthogonally applied current signals. Three processing channels are used to separate out the three components as x, y and z signals, from which calculations are made for determination of the three-dimensional location of the catheter tip within the body. An easy calibration procedure, which can be performed separately or during the mapping, is used to calibrate the system and provide the correlations between respective x, y and z sense signals and dimensional locations.

SUMMARY OF THE INVENTION

An embodiment of the present invention provides a method including, in a calibration phase, positioning a calibration-tool, including (a) a mapping-electrode and (b) a sensor of a location-measuring system, in an organ of a patient. The calibration-tool is tracked at different positions in the organ using the location-measuring system. A set of calibration data points at the respective different positions is generated, each calibration data point including signal-values obtained using the mapping-electrode and a corresponding position measurement of the sensor by the location-measuring system. The method further includes, in an investigation phase that is subsequent to the calibration phase, positioning an investigation-tool, having a mapping-electrode but no sensor of the location-measuring system, at a location in the organ of the patient. The signal-values at the location are measured using the mapping-electrode of the investigation-tool. Using a subset of the calibration data points, coordinates of the location are determined by deriving a respective nonlinear relation between (a) the signal-values obtained using the mapping-electrode of the investigation-tool and (b) the coordinates of the location and solving the nonlinear relation.

In some embodiments, the method includes solving a set of cubic equations.

In some embodiments, the method includes measuring the intrabody locations using a catheter-based magnetic location-tracking system.

In an embodiment, the method includes measuring one of voltages and impedances.

There is additionally provided, in accordance with an embodiment of the present invention, a system, including an interface and a processor. The interface is configured to communicate with a calibration-tool and with an investigation-tool, both configured to be inserted into an organ of a patient. The calibration tool includes a mapping-electrode and a sensor of a location-measuring system, and the investigation-tool includes mapping-electrode but no sensor of the location-measuring system. The processor is configured, in a calibration phase, to track the calibration-tool at different positions in the organ using the location-measuring system, and generate a set of calibration data points at the respective different positions, each calibration data point including signal-values obtained using the mapping-electrode and a corresponding position measurement of the sensor by the location-measuring system. The processor is further configured to, in an investigation phase that is subsequent to the calibration phase, measure the signal-values at a location using the mapping-electrode of the investigation-tool, and using a subset of the calibration data points, determine coordinates of the location by deriving a respective nonlinear relation between (a) the signal-values obtained using the mapping-electrode of the investigation-tool and (b) the coordinates of the location, and solving the nonlinear relation.

The present invention will be more fully understood from the following detailed description of the embodiments thereof, taken together with the drawings in which:

DETAILED DESCRIPTION OF EMBODIMENTS

Overview

Figure 1:
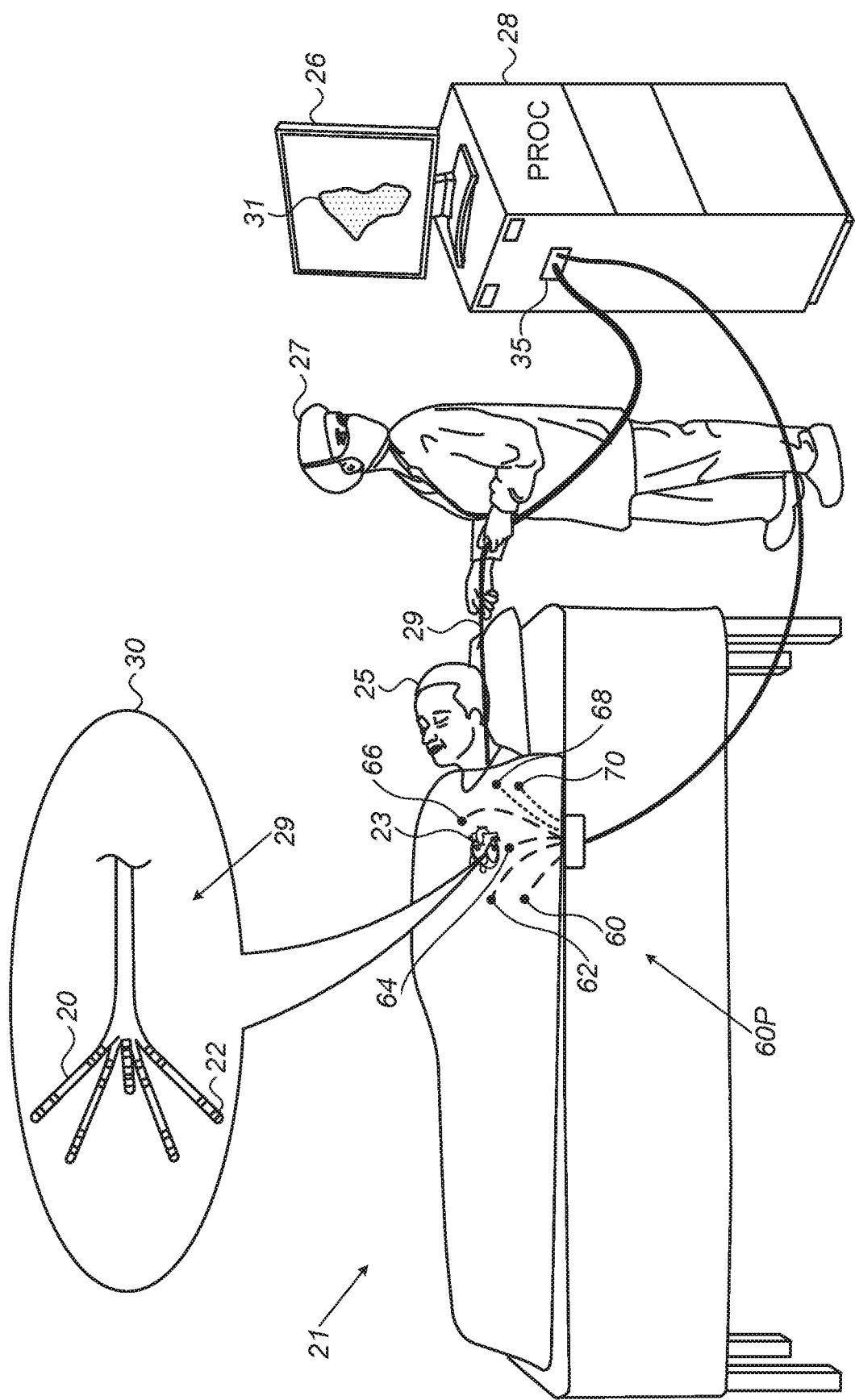
FIG. 1 is a schematic, pictorial illustration of a catheter-based system for electro-anatomical mapping, in accordance with an embodiment of the present invention.

Intrabody tissue is typically electrically conductive, which causes electric fields inside the body to vary, generally in a nonlinear way, with intrabody location. Despite this well-established observation, catheter-based location-tracking systems, and methods that are based on acquisition of electrical location signals (named also hereinafter "signal-values"), may employ an approximate description of electric fields as locally linearly dependent on intrabody locations. The linearization may be done for various reasons, such as to employ a linearized calibration model. To correct for inaccuracies that result from a local linearity assumption, electric signal-based location-tracking systems may employ methods of local calibrations as well as other computational efforts, such as interpolations and extrapolations.

Embodiments of the present invention that are described hereinafter provide a method to nonlinearly determine, based on electrical signal-values, a location inside an organ of a patient. To determine a location, a processor derives a set of nonlinear equations that connect between three coordinate-variables of the location and signal-values that an investigation-tool, such as an investigation-catheter measures at the location. The processor then solves the nonlinear equations (also named hereinafter "a nonlinear relation") to determine the location, as described below.

Examples of electric signal-based location-tracking systems that may employ the disclosed nonlinear location-tracking method are:

(I) Carto®3 (made by Biosense-Webster), in which the electrical signal-values are impedances measured between a mapping-electrode of a catheter and surface-electrodes; and (II) Carto®4 (made by Biosense-Webster), in which the electrical signal-values are voltages measured by a mapping-electrode.

In an embodiment used by way of example henceforth, the derived set of nonlinear equations are cubic and contains nine coefficients (i.e., unknowns) that the processor calculates based on a calibration.

For the calculation, during a calibration phase, a calibration-tool, such as a calibration-catheter, comprising (i) a mapping-electrode and (ii) a sensor of a location-measuring system, is inserted by a physician into the organ. The location-measuring system tracks the calibration-tool at different positions in the organ. The processor generates a set of calibration data points at the respective different positions, each calibration data point comprising signal-values (also named hereinafter "calibration signals"), obtained using the mapping-electrode, and a corresponding position measurement of the sensor by the location-measuring system such as a magnetic position-sensing or on medical imaging. In some embodiments, a processor stores one or more previously acquired set of calibration data-points.

During a subsequent tracking session (e.g., during an investigative invasive procedure, or phase), the processor estimates a location of the distal end of the investigation-catheter, for example, inside a cardiac chamber, by deriving and solving nonlinear relation based on a subset of the calibration data-points. The processor determines the coordinates of the location by deriving a respective nonlinear relation between (i) the signal-values obtained using the mapping-electrode of the investigation-tool and (ii) the coordinates of the location, and by solving the nonlinear relation, as described below.

The disclosed nonlinear derivation and solution method of a location in an organ is superior to deriving and solving a linear relation, which due to the linearity assumption, might be inherently less accurate. The disclosed nonlinear calibration technique thus provides a direct, less cumbersome, location tracking approach for use with electrical signal-based location-tracking systems. Nonlinear calibration may therefore simplify and shorten the duration of catheterization procedures while obtaining a more accurate location of an invasive probe.

System Description

FIG. 1 is a schematic, pictorial illustration of a catheter-based system 21 for electro-anatomical mapping, in accordance with an embodiment of the present invention. FIG. 1 depicts a physician 27 using an electro-anatomical investigation-catheter 29 to perform an electro-anatomical mapping of a heart 23 of a patient 25. As seen in inset 30, investigation-catheter 29 comprises at its distal end five arms 20, where several mapping-electrodes 22 are fitted at each arm 20. Arms 20 may be mechanically flexible. An example of this type of investigation-catheter is the Pentary® catheter (made by Biosense-Webster, Irvine Calif.).

Six surface electrodes are attached to the skin of the patient, which are named hereinafter patches 60, 62, 64, 66, 68, and 70, or collectively patches 60P. During an investigative electro-anatomical mapping procedure, modulated voltages are applied between pairs of patches 60P. Mapping-electrodes 22 measure resulting signal-values in the form of voltages in heart 23. The measured voltages are indicative of a location of each of mapping-electrodes 22 in heart 23. A processor 28 receives the measured signal-values from each mapping-electrode 22 via an electrical interface 35 and uses the signals to calculate the location of each mapping-electrode 22 in the heart. During and/or following the procedure, processor 28 may display an electro-anatomical map 31 on a display 26.

In some embodiments, catheter-based system 21 is calibrated using another, more accurate system, such as a magnetic location-measuring (not shown). During a calibration phase, a calibration-catheter (not shown) is inserted by the physician into a chamber of heart 23 of patient 25. The calibration-catheter comprises a mapping-electrode and a magnetic location sensor. The mapping-electrode measures voltages induced by patches 60P (i.e., calibration signals in the form of voltages). In parallel, in response to magnetic fields from external field generators, magnetic location signals from the magnetic sensor are received at processor 28. Based on the measured magnetic location signals, processor 28 calculates a location of the calibration-catheter in the heart.

The method of location-tracking using external magnetic fields is implemented in various medical applications, for example, in the CARTO™ catheter-based magnetic location-tracking system, produced by Biosense Webster and described in detail in U.S. Pat. Nos. 5,391,199, 6,690,963, 6,484,118, 6,239,724, 6,618,612, 6,332,089, 7,756,576, 7,869,865, 7,848,787, 7,848,789 and in PCT Patent Publication WO 96/05768, and in U.S. Patent Application Publications 2002/0065455 A1, 2003/0120150 A1 and 2004/0068178 A1, whose disclosures are all incorporated herein by reference.

An example of an electrical signal-based location system that can be magnetically calibrated is the Carto®4 (made by Biosense-Webster). Techniques covered by the Carto®4 system are described, for example, in U.S. patent application Ser. No. 15/966,514, filed Apr. 30, 2018, entitled "Improved Active Voltage Location (AVL) Resolution," which is assigned to the assignee of the present patent application and whose disclosure is incorporated herein by reference.

As noted above, in some embodiments of the present invention, processor 28 is configured to derive and solve a nonlinear relation, such as a cubic relation, between investigative signal-values and respective coordinates of a location at which the signals were measured by catheter 29. By deriving and solving a nonlinear relation, processor 28 accurately estimate, from electrical signals, an exact location of investigation-catheter 29 in heart 23, as described below.

The example illustration shown in FIG. 1 is chosen purely for the sake of conceptual clarity. Embodiments of the present invention may apply to any location sensing method that utilizes measured intrabody electrical signals. An example of another method of an electrical signal-based location-tracking system is one that uses currents instead of voltages, known as ACL (Active Current Location). The ACL method uses currents injected by electrode 32 to measure impedances between a mapping-electrode and a number of body surface electrodes (instead of using electrode 32 to sense voltages). Based on the measured impedances, the system tracks the location of the mapping-electrode within the body. Details of the ACL method are described in U.S. Pat. No. 8,456,182, whose disclosure is incorporated herein by reference. The ACL method is used, for example, in the CARTO®3 system (made by Biosense-Webster).

Other types of sensing and/or therapeutic catheters, such as the multi-electrode Lasso® Catheter (produced by Biosense Webster) may equivalently be employed while using embodiments of the present invention. Similarly, multi-electrode basket catheters may benefit from using the disclosed technique for location-tracking. Other types of electrodes, such as those used for ablation, may be utilized in a similar way for electrodes 22 to acquire location signals. Thus, an ablation electrode used for collecting electrical signals is regarded as a useable mapping-electrode.

Processor 28 typically comprises a general-purpose computer with software programmed to carry out the functions described herein. The software may be downloaded to the computer in electronic form, over a network, for example, or it may, alternatively or additionally, be provided and/or stored on non-transitory tangible media, such as magnetic, optical, or electronic memory.

Nonlinear Electric Field Location System

Figure 2:
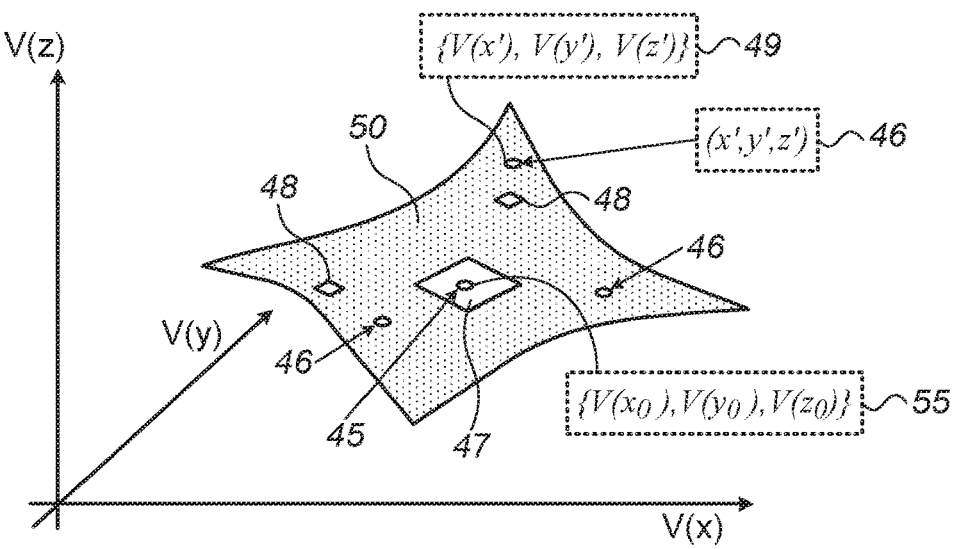
FIG. 2 is a schematic illustration of a nonlinear cubic relation between signal-values and a respective location, in accordance with an embodiment of the present invention.

FIG. 2 is a schematic illustration of a nonlinear relation 50 between signal-values and a respective location, in accordance with an embodiment of the present invention. Nonlinear cubic relation 50 is obtained by processor 28 by deriving and solving a set of cubic equations, given by Eq. 1, connecting signals-values 55, $\{V(x_0), V(y_0), V(z_0)\}$, measured by investigation-catheter 29 at a given location 45, and the coordinate of location 45, $(x_0, y_0, z_0)$.

$$\begin{cases} V(x; \omega_x) = a_{1x}x + a_{2x}x^2 + a_{3x}x^3 \\ V(y; \omega_y) = a_{1y}y + a_{2y}y^2 + a_{3y}y^3 \\ V(z; \omega_z) = a_{1z}z + a_{2z}z^2 + a_{3z}z^3 \end{cases} \quad \text{Eq. 1}$$

As seen, Eq. 1 includes nine unknown coefficients $a_{ij}$, which connect a location (x, y, z) to a set of modulated electrical signal-values, e.g., voltages $\{V(x; \omega_x), V(y; \omega_y), V(z; \omega_z)\}$. For example, $\{V(x; \omega_x), V(y; \omega_y), V(z; \omega_z)\}$ are voltages measured by mapping electrode 22 of catheter 29 while catheter 29 is being tracked by the Carto®4 system described above. To find coefficients $a_{ij}$, the processor uses a subset of three data points, where each data point comprises calibration voltages 49, $\{V(x'), V(y'), V(z')\}$, measured at a magnetically measured locations 46, (x', y', z'). As noted above, such sub-set is chosen from a set of data points that were measured with a calibration-tool during calibration. Substituting the three data points in Eq. 1, processor 28 solves resulting inhomogeneous matrix equations to extract a unique solution consisting of coefficients $a_{ij}$.

Substituting $\{V(x_0), V(y_0), V(z_0)\}$ in the derived Eq. 1 (i.e., with the derived coefficients $a_{ij}$), processor 28 yields three cubic polynomial equations, one for each of the coordinates of $\{V(x_0), V(y_0), V(z_0)\}$. Processor 28 solves the cubic equations, which has a physical solution, to obtain the location of investigation-catheter 29 in the heart.

The above nonlinear method for location tracking is applicable also to multiple mapping-electrodes. In an embodiment, all locations of mapping-electrodes about a given location of one of the electrodes (typically a one close to an average location that the multiple mapping-electrodes define) are calculated using a single set of coefficients $a_{ij}$. In an embodiment, a spatial extent to which nonlinear relation 50 is useful for finding multiple locations without deriving a new set of Eq. 1, is evaluated empirically, for example, by comparing a location derived using Eq. 1 with one measured magnetically and not used for solving Eq. 1.

In an optional embodiment, the relative locations of multiple mapping-electrodes 22 is be further improved based on a known geometry of the catheter, for example, by using geometrically known intra-electrode distances $D_{ij}$ between mapping-electrodes 22:

$$(u_i-u_j)^2+(v_i-v_j)^2+(w_i-w_j)^2=D_{ij}^2 \quad \text{Eq. 2}$$

where $(u_i, v_i, w_i)$ and $(u_j, v_j, w_j)$ are spatial coordinates of respective mapping-electrodes 22i and 22j out of a given number M of multiple electrodes. Measuring sufficient electrical location-signals allows the substitution of sufficient data points to solve Eq. 2.

In some of the derivation steps of nonlinear linear relation 50 described above, more data points may be available than are required, and persons skilled in the art will select those best suited, for example, to maximize accuracy.

Finally, to illustrate the advantages of a nonlinear relation over a linear one, a local linear relation 47 (i.e., the solution of a set of the linear part of Eq. 1) is shown as well in FIG. 2. As seen, relation 47 establishes a very localized linearized relation. In addition, the nonlinear nature of the electric fields would require multiple computations to obtain other local linear relations 48 over surface 50 (seen as tiny local linear patches 48 that are embedded in global non-linear relation 50). This comparison demonstrates how the disclosed nonlinear technique provides a globally accurate and less complex location tracking scheme.

Figure 3:
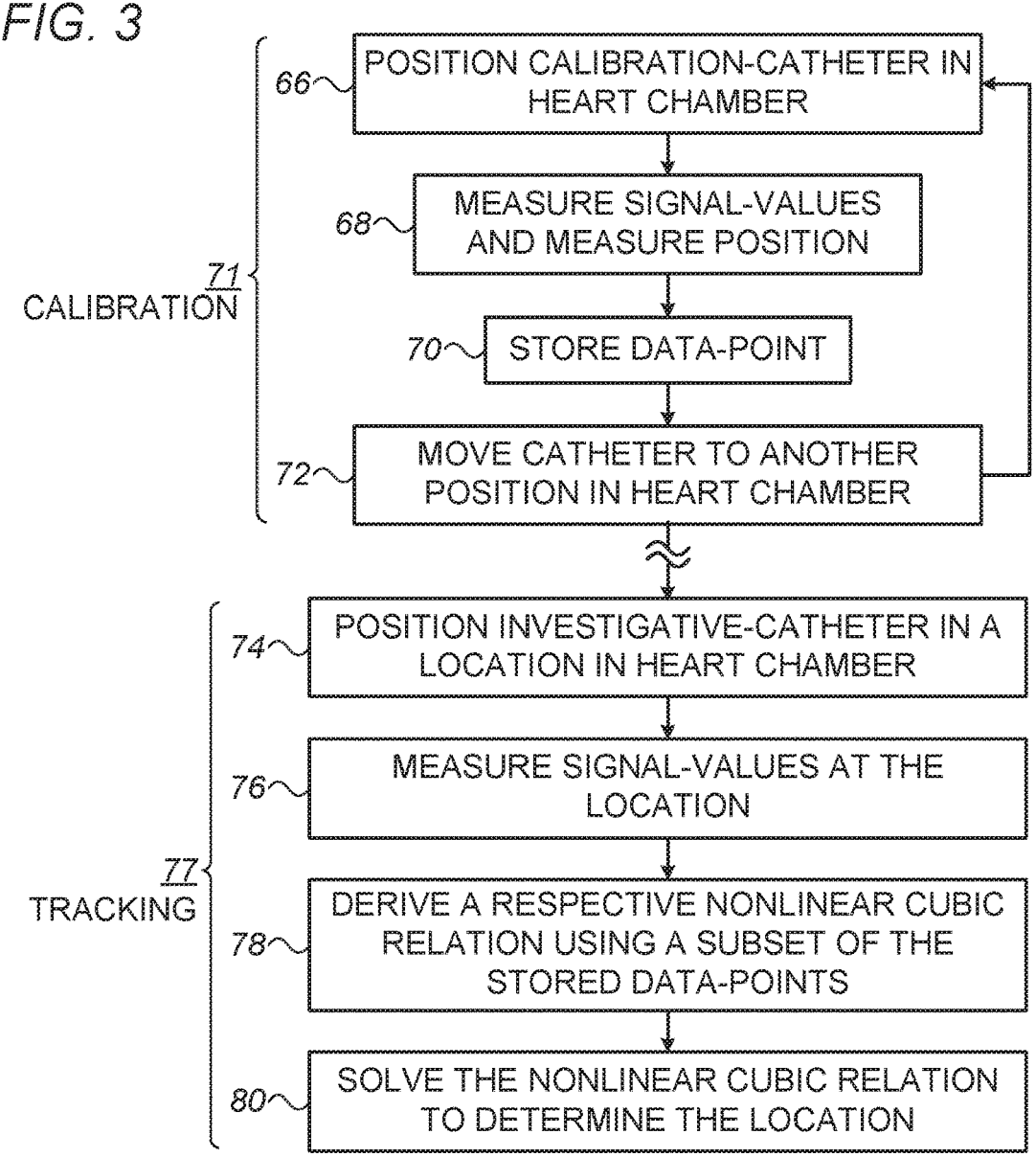
FIG. 3 is a flow chart that schematically illustrates a method for catheter-based location-tracking using the nonlinear relation shown in FIG. 2, in accordance with an embodiment of the present invention.

FIG. 3 is a flow chart that schematically illustrates a method for catheter-based location-tracking using the nonlinear relation shown in FIG. 2, in accordance with an embodiment of the present invention. The process is generally divided into a calibration phase 71, in which a set of calibration data-points is generated, and a tracking phase 77, in which, based on a sub-set of data-points, a nonlinear relation is derived and solved for tracking a location.

Calibration phase 71 begins with positioning of a calibration-catheter in a heart chamber, at a calibration-catheter positioning step 66. Next, the system measures signal-values at the position, for example by measuring impedances between a mapping-electrode and surface electrodes 60P, at a data point acquisition step 68. In parallel, the tracking system measures the position, for example, using a magnetic position-sensor, at the same data point acquisition step 68.

The electrically measured calibration signal-values and the respective magnetically measured position are saved by processor 28, at a data-point storage step 70. The calibration-catheter is repositioned in the heart chamber, at a calibration-catheter repositioning step 72, so as to acquire another data-point. Calibration phase 71 ends where the stored set of data-points is determined sufficient.

Tracking phase 77 begins with positioning of investigation-catheter 29 at a location in the heart chamber, at an investigation-catheter positioning step 74. Next, the tracking-system measures signal-values, e.g., impedances, between mapping-electrode 22 at the location and surface electrodes 60P, at a signal-values measurement step 76.

Next, at a nonlinear relation derivation step 78, processor 28 calculates a nonlinear relation, which, as described above, connects between signal-values measured at step 76 and the coordinates of the location.

Finally, processor 28 determines the location of mapping-electrode 22 by solving the derived nonlinear relation. The process may then continue by moving the investigation-catheter to another location and repeating steps 76-80.

The example flow chart shown in FIG. 3 is chosen purely for the sake of conceptual clarity. In alternative embodiments, the positions are measured during calibration phase by other means, such as with imaging and image registration techniques. Nevertheless, the principle of deriving and using the nonlinear relation to determine one or more location holds to other signal acquisition and processing methods and systems and is potentially superior to applying a linear relation.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method, comprising:
   (i) in a calibration phase:
      positioning a calibration-tool, comprising (a) a mapping-electrode and (b) a sensor of a location-measuring system, in an organ of a patient;
      tracking the calibration-tool at different positions in the organ using the location-measuring system; and
      generating a set of calibration data points at the different positions, each calibration data point comprising signal-values obtained using the mapping-electrode and a corresponding position measurement of the sensor by the location-measuring system; and
   (ii) in an investigation phase that is subsequent to the calibration phase:
      positioning an investigation-tool, having a mapping-electrode but no sensor of the location-measuring system, at a location in the organ of the patient;
      measuring signal-values at the location using the mapping-electrode of the investigation-tool; and
      using a subset of the calibration data points, determining coordinates of the location by deriving a respective nonlinear relation between (a) the signal-values obtained using the mapping-electrode of the investigation-tool and (b) the coordinates of the location, and solving the nonlinear relation,
   wherein solving the nonlinear relation comprises solving a set of cubic equations, wherein the set of cubic equations consists of:

$$V(x; \omega_x) = a_{1x}x + a_{2x}x^2 + a_{3x}x^3$$
   $$V(y; \omega_y) = a_{1y}y + a_{2y}y^2 + a_{3y}x^3$$
   $$V(z; \omega_z) = a_{1z}z + a_{2z}z^2 + a_{3z}x^3,$$

wherein the set of cubic equations includes nine unknown coefficients $a_{ij}$, which connect a location (x, y, z) to a set of modulated electrical signal-values, said modulated electrical signal values being voltages $\{V(x; \omega_x), V(y; \omega_y), V(z; \omega_z)\}$.

2. The method according to claim 1, wherein the location-measuring system comprises a catheter-based magnetic location-tracking system.

3. The method according to claim 1, wherein measuring the signal-values comprises measuring one of voltages and impedances.

4. A system, comprising:
   an interface, configured to communicate with a calibration-tool and with an investigation-tool, both configured to be inserted into an organ of a patient, wherein the calibration tool comprises a mapping-electrode and a sensor of a location-measuring system, and wherein the investigation-tool comprises mapping-electrode but no sensor of the location-measuring system; and
   a processor, configured to:
      (i) in a calibration phase:
         track the calibration-tool at different positions in the organ using the location-measuring system; and
         generate a set of calibration data points at the different positions, each calibration data point comprising signal-values obtained using a mapping-electrode and a corresponding position measurement of the sensor by the location-measuring system; and
      (ii) in an investigation phase that is subsequent to the calibration phase:
         measure signal-values at a location using the mapping-electrode of the investigation-tool; and
         using a subset of the calibration data points, determine coordinates of the location by deriving a respective nonlinear relation between (a) the signal-values obtained using the mapping-electrode of the investigation-tool and (b) the coordinates of the location, and solving the nonlinear relation, wherein solving the nonlinear relation comprises solving a set of cubic equations, wherein the set of cubic equations consists of:

$$V(x; \omega_x) = a_{1x}x + a_{2x}x^2 + a_{3x}x^3$$

$$V(y; \omega_y) = a_{1y}y + a_{2y}y^2 + a_{3y}x^3$$

$$V(z; \omega_z) = a_{1z}z + a_{2z}z^2 + a_{3z}x^3,$$

wherein the set of cubic equations includes nine unknown coefficients $a_{ij}$, which connect a location (x, y, z) to a set of modulated electrical signal-values, said modulated electrical signal values being voltages $\{V(x; \omega_x), V(y; \omega_y), V(z; \omega_z)\}$.

5. The system according to claim 4, wherein the location-measuring system comprises a catheter-based magnetic location-tracking system.

\* \* \* \* \*